United States Patent [19]

Lipowski

[11] 4,245,994
[45] Jan. 20, 1981

[54] WATER SOLUBLE POLYMERIC TEXTILE TREATING AGENT

[75] Inventor: Stanley A. Lipowski, Livingston, N.J.

[73] Assignee: Diamond Shamrock Corporation, Dallas, Tex.

[21] Appl. No.: 820,120

[22] Filed: Jul. 29, 1977

[51] Int. Cl.$^3$ .............................................. D06P 5/02
[52] U.S. Cl. ............................................ 8/74; 8/531; 8/587
[58] Field of Search ................... 8/74, 165, 21 B, 89 R

[56] References Cited

U.S. PATENT DOCUMENTS

| 3,790,344 | 2/1974 | Frickenhaus | 8/173 |
| 3,961,881 | 6/1976 | Sumner | 8/65 |

FOREIGN PATENT DOCUMENTS

| 742126 | 7/1963 | Canada | 8/74 |
| 283401 | 10/1952 | Switzerland . | |

OTHER PUBLICATIONS

Color Index, vol. 4, 3rd Edition, p. 4003.

*Primary Examiner*—Joseph L. Schofer
*Assistant Examiner*—Maria S. Tungol
*Attorney, Agent, or Firm*—Leslie G. Nunn, Jr.

[57] ABSTRACT

Washfastness of dyed nylon textile material is improved by treating dyed textile material with a water soluble polymeric textile treating agent which is a reaction product of dihydroxy diphenyl sulfone, formaldehyde and naphthalenesulfonic acid and is characterized as a 30% by weight solution in acetone having a reduced viscosity at 21° C. of between about 0.225 and about 0.275.

9 Claims, No Drawings

WATER SOLUBLE POLYMERIC TEXTILE TREATING AGENT

BACKGROUND OF THE INVENTION

1. Field of the Invention

This invention relates to a process of improving washfastness of dyed nylon textile materials by treatment with water soluble polymeric textile treating agents.

2. Description of the Prior Art

In the dyeing of nylon textile materials, acid dyes selected for minimum barre' and warpiness often have poor washfastness. Washfastness of dyed material may be improved by back tanning, i.e., treatment with 1 to 2% tannic acid and 1 to 2% of 85% formic acid at 70° C. for 15 to 20 minutes; 1 to 2% tartar emetic is then added and treatment continued for an additional 15 to 20 minutes at 70° C. A simpler procedure involves contacting dyed material with a liquor containing 3 to 5% of a phenolic derivative such as Cibatex PA, Tanninol WR or Nylofix P and 2% of 85% formic acid for 15 to 30 minutes at 70° to 90° C.

Swiss 283,402—G. R. Geigy, A.G. shows use of synthetic tanning agents as reserving agents for polyamide or polyurethane fibers in blends with wool or silk. These agents are prepared by acid condensation of naphthalenesulfonic acid, dihydroxy diphenyl sulfone and formaldehyde using these components at molar ratios such as 1:1:1, 1:1.5:1 and 1:0.7:0.75. They can be added to the dyebath or used to pretreat textile materials which are then rinsed and dyed. Additional information may be found in *Chemical Abstracts* 47, 10861i (1953). A similar product, Erional NW, is described in the 1965 Technical Manual of the American Association of Textile Chemists and Colorists on page E-140. This product is a mixed condensate of naphthalene monosulfonic acids with dihydroxy diphenylsulfones and formaldehyde which is used as a reserving agent on nylon and a fixative for certain acid colors on nylon.

U.S. Pat. No. 3,790,344—Frickenhaus et al, Feb. 5, 1974 shows washfastness of dyed synthetic polyamide textile material may be improved by aftertreating dyed material with condensation products which are barely water-soluble higher molecular weight polymers prepared in aqueous medium using dihydroxy diphenyl sulfone, formaldehyde and naphthalenesulfonic acid using components in molar ratios of 1:0.7–1.1:0.7–0.2. These condensation products are reported to be better than water soluble tanning agents (water soluble condensation products of dihydroxy diphenyl sulfone, formaldehyde and naphthalenesulfonic acid) in improving washfastness, but they are not useful as tanning agents because they can only be dissolved in hot water and form opalescent solutions.

STATEMENT OF THE INVENTION

Washfastness of dyed nylon textile materials and cotton blends thereof is improved by treating the dyed textile material with a water soluble polymeric textile treating agent in an amount sufficient to improve washfastness wherein the textile treating agent is a reaction product of dihydroxy diphenyl sulfone, formaldehyde and naphthalenesulfonic acid and is characterized as a 30% by weight solution in acetone having a reduced viscosity at 21° C. of between about 0.225 and about 0.275. A useful treating agent may be prepared by reacting one mole of dihydroxy diphenyl sulfone with from about 0.85 to about 1.10 mole of formaldehyde and from about 0.9 to about 1.1 mole of naphthalenesulfonic acid.

DESCRIPTION OF THE PREFERRED EMBODIMENTS

The water soluble polymeric textile treating agent is added in an amount sufficient to improve washfastness. From about 1 to about 5% of the agent owf (on weight of fiber) is added to the exhausted dyebath after the rinse and run for about 20 to about 30 minutes at about 190° F. to about 200° F. The pH of the bath should be adjusted to about 5 by adding from about 1 to about 3% by weight acetic acid solution. After this treatment, the goods are rinsed well. If desired, a softener is added. The rinsed goods are then dried.

In an aftertreatment of deep shades using acid dyestuffs having very poor fastness properties, quality of the dyeing may be improved by finishing off the dyeing cycle with the addition of about 1 to about 3% tannic acid owf at about 100° F. and then raising the temperature to about 160° F. to about 180° F. at a rate of about 3° F. per minute. Then about 3 to about 5% treating agent owf is added as an aftertreatment and the bath is held for about 20 to 30 minutes at about 160° F. to about 180° F. Then the goods are rinsed well and dried.

When these water soluble polymeric textile treating agents are used in the aftertreatment of acid dyed nylon textile materials to improve washfastness and reduce crocking, they may be applied to a variety of nylon textile materials including yarn, woven or knit goods and carpeting. The textile material may be dyed or printed. It is to be understood that the term nylon textile material as used herein encompasses all types of nylon textiles as well as nylon blends with cotton. When acid dyes selected for minimum barre' and warpiness' on filament nylon do not have the required fastness to washings, perspiration and water bleeding, their shortcomings may be overcome by use of these water soluble polymeric agents in the aftertreatment processes described herein.

Suitable water soluble polymeric textile treating agents are prepared by reacting dihydroxy diphenyl sulfone, formaldehyde and naphthalenesulfonic acid to obtain reaction products which can be characterized as 30% by weight solutions in acetone having a reduced viscosity at 21° C. of from about 0.225 to about 0.275. Suitable reaction products may be obtained by reacting 1 mole of dihydroxy diphenyl sulfone with from about 0.85 to about 1.10 mole of formaldehyde and from about 0.9 to about 1.1 mole of naphthalenesulfonic acid. For example, these polymeric treating agents may be prepared by mixing one mole of sulfone with from about 0.95 to about 1.00 moles naphthalenesulfonic acid in water to obtain a uniform mixture, heating the mixture to 100° C., then cooling to 25°–50° C. and adding from about 0.90 to about 0.95 moles of formaldehyde. Sufficient water should be added to obtain a concentration of 55 to 70% solids in the reaction mixture. The reaction mixture may then be heated to reflux and refluxed for about 10 to 20 hours to obtain a reaction product having the specified reduced viscosity. If desired, a catalyst such as boron fluoride may be added to promote reaction. These treating agents are produced as free acids and used without neutralization.

The sulfone used in the preparation of these textile treating agents is dihydroxy diphenyl sulfone prepared from phenol and sulfuric acid by any known method.

The procedure described in Example I (A) is preferred. It is to be understood that preparation of this sulfone from phenol is well known in the art and that this invention is not to be limited to agents based on the sulfone procedure described in the examples.

Formaldehyde or formaldehyde liberating compositions can be used in the preparation of the textile treating agents disclosed in the present invention. For example, formaldehyde can be used in the form of 10% to 40% aqueous solutions, 30% to 55% alcohol solutions with alcohols such as methanol, n-butanol, i-butanol or the like. Formaldehyde can also be used in the form of a formaldehyde liberating composition such as para-formaldehyde, trioxane, or other polymeric forms. It is also to be understood that such formaldehyde liberating compositions include forms such as acetals capable of producing formaldehyde.

Naphthalenesulfonic acid used in the preparation of the textile treating agents may be prepared by any known method but the method described in Example I (B) is preferred. Since naphthalenesulfonic acid is a well known product, it is to be understood that this invention is not to be limited to agents based on the naphthalenesulfonic acid procedure used in the examples.

Viscosity of these textile treating agents in a 30% by weight acetone solution is determined using the Hoeppler Viscosimeter. Operating on the falling ball principle, this viscosimeter measures absolute viscosity of a fluid from a measurement of the time required for a ball, made of glass or of special steel, to fall through a column of the fluid sample enclosed in a precision glass tube. Bore of tube is about 16 mm and length about 200 mm.

This measurement is made by timing fall of the ball through the accurately calibrated distance between two marks on the glass tube. The absolute viscosity is obtained by multiplying the time interval by a factor involving temperature, specific gravity of the fluid, and a constant characteristic of the ball used in the following formula:

$$c_\eta = T \times (S_b - S_f) \times B,$$

wherein
- $c_\eta$ = absolute viscosity in centipoises
- T = time interval of the falling ball
- $S_b$ = specific gravity of the ball
- $S_f$ = specific gravity of the fluid at the measuring temperature
- B = ball constant
- ($S_b$ and B are from in the calibration certificate supplied by the manufacturer).

If the time interval is measured by a stopwatch with an accuracy of 0.02 seconds, ultimate accuracy of the measurement is 0.1%. If the temperature of the water in the glass jacket is maintained precisely at 21° C., the usual range of viscosities (10 to 600 centipoises) can be determined with an accuracy of 0.1%, and the extremities of the range within 0.5%.

Reduced viscosity ($\eta_{red}$) of a 30% by weight of the textile treating agent in acetone solution may be determined using the following equations:
- $c_o$ = 0.332 cps solvent viscosity (acetone)
- $c_\eta$ in cps Hoeppler viscosity of acetone solution
- $\eta_r = c_\eta/c_o$ relative viscosity
- $\eta_{sp} = \eta_r - 1$ specific viscosity
- $\eta_{red} = \eta sp/c$ reduced viscosity wherein c = concentration (30%)

For a fuller understanding of the nature and objects of this invention, reference may be made to the following examples which are given merely to illustrate the invention and are not to be construed in a limiting sense. All weights, proportions and percentages are by weight unless otherwise indicated. Likewise, all temperature are °C. unless otherwise indicated. The term of means on weight of fiber.

EXAMPLE I

This example describes preparation of a textile treating agent within the scope of this invention.

A. Preparation of a sulfone from phenol 1168 g phenol (12.41 m) and 620 g sulfuric acid 98% (6.19 m) were charged under a nitrogen blanket into a glass lined reactor equipped with agitator, condenser and separator for water and solvent. The mixture was agitated and heated to 145° C. After heating 30 minutes at 145° C., 153 g of monochlorobenzene was added and the mixture cooled to 140° C. When heating was resumed, a high rate of reflux was maintained while water was being separated from solvent in the separator and solvent was being returned to the reactor. As reaction proceeded, the reflux temperature gradually rose to a maximum of 170° C. A total of 215 g of water was separated during the 15 hour reflux. A 10 g sample was taken from the reaction mixture; dispersed in 100 ml distilled water and then titrated with 19 ml of 0.5 N sodium hydroxide to a pH of 6.5 using a pH meter.

The separator was then disconnected; nitrogen flow was stopped and the condenser set to return reflux. A solution containing 154 g sodium hydroxide 50% and 1061 g water was then added slowly under good agitation while the reaction mixture was being cooled to 95° C. The separator was reconnected; the reaction mixture heated to reflux and solvent removed azeotropically over 3 hours. A clear red colored aqueous solution boiling at 101° C. was obtained. This solution of the sodium salt of the sulfone was cooled to 95° C. and 23 g of sodium hydrosulfite was added in 3 portions over 10 minutes. The solution was then refluxed for 10 minutes. During reflux, color of the solution changed from red to orange.

The hot orange solution was charged to a stainless steel reactor containing a solution of 923 g sodium hydroxide 50% in 6290 g water to obtain 10,000 g of an alkaline solution having a pH of 10.5. This solution remained clear on cooling to 25° C. A solution of 600 g of sulfuric acid 98% in 1200 g water was added slowly under rapid agitation to the alkaline solution to precipitate the sulfone and form a slurry of the sulfone. The resulting sulfone slurry had a pH of 3.5.

Sulfone was separated from the slurry by centrifuging the slurry. The sulfone washed in the centrifuge until the wash water was free of sulfate ions, i.e., it remained clear and did not become cloudy when 0.1 N barium chloride solution was added. After removal of the sulfone from the centrifuge in the form of a paste, it was dried in a fluidized bed drier, and then ground to a fine powder. A total of 1000 g of dry, off white colored dihydroxy diphenyl sulfone was obtained having the following properties:

| | |
|---|---|
| pH (5% slurry in distilled water): | 4.4 |
| Melting Point (Fisher Johns): | 230–246° C. |
| Differential Scanning Calorimetry: | Major Peak 230° C. |

|                |                        |
| -------------- | ---------------------- |
| Ash:           | 0.1%                   |
| Assay:         | 98.5% 4,4'isomer       |

B. Preparation of naphthalenesulfonic acid 500 g naphthalene (3.9 m) and 624 g sulfuric acid 98% (6.23 m) were charged to a reactor and mixed. The resulting mixture was then heated rapidly to 150° C. and agitated at 150° C. for 3 hours to obtain 1080 g of naphthalenesulfonic acid having the following properties:

|                               |       |
| ----------------------------- | ----- |
| Free Oil:                     | 0.2%  |
| Naphthalene disulfonic acid:  | 3.1%  |
| Naphthalene monosulfonic acid:| 72.5% |
| Free sulfuric acid:           | 20.2% |
| Water:                        | 4.0%  |
| Acid value:                   | 404   |

C. Preparation of a textile treating agent 1000 g of dry sulfone (4 m) from Example I (A) above, 800 g water and 1080 g naphthalenesulfonic acid (3.9 m) from Example I (B) above were charged to a reactor and mixed to obtain a uniform mixture. This mixture was heated to 100° C., then cooled to 50° C. and 328 g 37% formaldehyde solution (4 m) added. The mixture of sulfone, acid and formaldehyde was heated to reflux which began at 108° C. and refluxed for 15 hours. Temperature at the end of the reflux period was 110° C. During reflux, color of the reaction mixture changed from dark brown to cherry red. At the end of the reflux period, heating was discontinued and 800 g water added to the agitated reaction mixture to obtain 4000 g of a cherry red viscous solution having the following properties:

| Solids:                          | 52.0%                                   |
| -------------------------------- | --------------------------------------- |
| pH 2% solution:                  | 1.6                                     |
| Viscosity:                       | 3000 cps, Brookfield, Spindle No. 3 at 30 RPM, 25° C. |
| Solidification Point:            | 20–30° F.                               |
| Acid value:                      | 110 as is                               |
| Reduced Viscosity $n_{sp}/c$ in acetone solution at 21° C.: | 0.241 Hoeppler Viscosity of 30% by weight acetone solution of dried solids |
| Ratio Sulfone: NSA: Formaldehyde: 1:0.975:1 | |

The acetone solution used in the reduced viscosity measurement contained 30% by weight dried solids obtained by evaporating the solution of textile treating agent to dryness to obtain the dried solids which were then dissolved in acetone.

EXAMPLE II

This example describes preparation of a textile treating agent within the scope of this invention.

A. Preparation of a sulfone from phenol

Dihydroxy diphenyl sulfone was prepared by the procedure given in Example I (A).

B. Preparation of naphthalenesulfonic acid 128 g naphthalene (1.0 m) and 160 g sulfuric acid 98% (1.6 m) were charged to a reactor and mixed. This mixture was heated rapidly to 150° C. and agitated at 150° C. for 4 hours to obtain a naphthalenesulfonic acid having an acid value of 408.

C. Preparation of a textile treating agent 250 g of dry sulfone (1 m) from Example II (A) above, 200 g water and naphthalenesulfonic acid (1.0 m) from Example II (B) above were charged to a reactor, mixed until uniform and then heated to 100° C. The heated reaction mixture was cooled to 23° C. and 81 g 37% formaldehyde solution (1.0 m) added. Then 33 g $BF_3(C_2H_5)O$ (0.23 m) was added as a catalyst and this mixture was heated to reflux which began at 83° C. The mixture was refluxed for 24 hours. At the end of the reflux period, temperature of the mixture was 110° C. During reflux, color of the reaction mixture changed from dark brown to cherry red. The reaction mixture was diluted with 200 g water and agitated to obtain about 1000 g of a cherry red viscous clear solution having the following properties:

| Solids:                          | 52.3%                                   |
| -------------------------------- | --------------------------------------- |
| pH 2% solution:                  | 1.7                                     |
| Viscosity:                       | 3064 cps, Brookfield, Spindle No. 3 at 30 RPM, 25° C. |
| Reduced Viscosity $n_{sp}/c$ in acetone solution at 21° C.: | 0.240 Hoeppler Viscosity of 30% by weight acetone solution of dried solids |
| Ratio Sulfone: NSA: Formaldehyde: 1:1:1 | |

EXAMPLE III

This example describes preparation of a textile treating agent outside the scope of this invention using high acid and formaldehyde ratios.

A. Preparation of a sulfone from phenol

Dihydroxy diphenyl sulfone was prepared by the procedure given in Example I (A).

B. Preparation of naphthalenesulfonic acid 256 g naphthalene (2.0 m) and 200 g sulfuric acid 98% (2.0 m) were charged to a reactor and mixed. The mixture was then heated rapidly to 150° C. and agitated at 150° C. for 2 hours. Then 100 g sulfuric acid 98% was added and the mixture agitated for an additional hour to obtain the naphthalenesulfonic acid.

C. Preparation of a textile treating agent 250 g of dry sulfone (1.0 m) from Example III (A) above, 200 g water and the naphthalenesulfonic acid mixture from Example III (B) above were charged to a reactor, mixed to obtain a uniform mixture and then heated to 100° C. The heated mixture was then cooled to 50° C. and 162 g 37% formaldehyde solution (2.0 m) and 50 g sulfuric acid 98% added. This mixture was heated to 90° C. and then held at 90° C. for 37 hours. Color of the reaction mixture changed from dark brown to cherry red. The reaction mixture was diluted with 800 g water and agitated to obtain about 2000 g of a cherry red viscous solution having the following properties:

| Solids:    | 45.3%               |
| ---------- | ------------------- |
| Viscosity: | 960 cps, Brookfield, |

-continued

| | |
|---|---|
| Reduced Viscosity $n_{sp}/c$ in acetone solution at 21° C.: | Spindle No. 3 at 30 RPM, 25° C. 0.193 Hoeppler Viscosity of 30% by weight acetone solution of dried solids |
| Ratio Sulfone: NSA: Formaldehyde: 1:2:2 | |

EXAMPLE IV

This example describes preparation of a textile treating agent outside the scope of this invention using low acid and formaldehyde ratios.

A. Preparation of a sulfone from phenol

Dihydroxy diphenyl sulfone was prepared by the procedure given in Example I (A).

B. Preparation of naphthalenesulfonic acid 89.6 g naphthalene (0.7 m) and 70 g sulfuric acid 98% (0.7 m) were charged to a reactor and mixed. The mixture was then heated rapidly to 150° C. and agitated at 150° C. for 2 hours. Then 30 g sulfuric acid 98% (0.3 m) was added and agitated for an additional hour at 150° C.

C. Preparation of a textile treating agent 250 g of dry sulfone (1.0 m) from Example IV (A) above, 100 g water and the acid mixture from Example IV (B) above were charged to a reactor, mixed until uniform and then heated to 100° C. The heated reaction mixure was then cooled to 50° C. and 57 g 37% formaldehyde solution (0.7 m) added. This mixture was heated to reflux which began at 112° C. and then refluxed for 6 hours. At the end of the 6 hour reflux period, 50 g of water was distilled off from the reaction and the reaction mixture temperature rose to 120° C. The mixture was refluxed at 120° C. for 10 hours. During the 10 hour reflux period, the reaction mixture color changed from dark brown to cherry red. The reaction mixture was then diluted with 350 g water and agitated to obtain 895 g of a cherry red viscous solution having the following properties:

| | |
|---|---|
| Solids: | 49.8% |
| Visosity: | 300 cps, Brookfield, Spindle No. 3 at 30 RPM, 25° C. |
| Reduced Viscosity $n_{sp}/c$ in acetone solution at 21° C.: | 0.185 Hoeppler Viscosity of 30% by weight acetone solution of dried solids |
| Ratio Sulfone: NSA: Formaldehyde: 1:0.7:0.7 | |

EXAMPLE V

This example describes preparation of a textile treating agent outside the scope of this invention using cresol instead of phenol.

A. Preparation of a sulfone from ortho cresol 432 g (4 m) ortho cresol, 200 g (2 m) of sulfuric acid 98% (by weight) and 100 g monochlorobenzene were charged into a reaction vessel equipped with agitator, condenser and water separator. The reaction mixture was heated to reflux temperature. Reflux began at about 130° C. Escaping vapors of chlorobenzene and water formed during the reaction were condensed, collected and separated in the water separator. The chlorobenzene, the bottom layer of the two phases in the separator, was returned to the reaction mixture and water, the upper layer, was removed, measured and discarded. Reaction temperature was gradually increased to 155° C. At the end of the reaction, a total of 72 g water was removed from the reaction mixture. A 10 g sample of the reaction mixture was taken and neutralized to a pH of 7.0 with 0.5 N sodium hydroxide solution. Neutralization of the sample required 13 ml of the solution. The water separator was disconnected at this point and the system set to full reflux. After all of the chlorobenzene was returned to the reaction mixture and the liquid temperature had dropped to about 140° C., 100 g water was added slowly to the reaction product and then 32 g of 50% by weight sodium hydroxide solution. Next 400 g of water was added; the water separator was reconnected to the system and chlorobenzene removed by azeotropical distillation. After all of the chlorobenzene was removed, the reaction product in the form of brick red colored crystals of dihydroxy dimethyl diphenyl sulfone was separated from the water by filtration, washed with water, removed from the filter and dried in an oven at 110° C. A total of 400 g of dihydroxy dimethyl diphenyl sulfone was recovered (about 70% of the theoretical yield).

B. Preparation of naphthalenesulfonic acid 128 g (1 m) of naphthalene and 160 g (1.6 m) of sulfuric acid 98% by weight were mixed together in a reaction flask. The resulting agitated reaction mixture was heated rapidly to 155° C. and was reacted for 3 hours at 155° C. to obtain a naphthalenesulfonic acid and sulfuric acid mixture. This mixture contained about 20% free sulfuric acid and solidified at about 80° C. The mixture was used either in solid or melted form.

C. Preparation of a textile treating agent 278 g (1 m) of sulfone from Example V (A) and 100 g water were charged to a reactor and slurried. Then 288 g (1 m) of naphthalenesulfonic acid from Example V (B) and 81 g formaldehyde 37% (1 m) were added and the resulting reaction mixture heated gradually to reflux temperature (110° C.) and was refluxed for 27 hours. Final reflux temperature was 110° C. Then 550 g of water was added and the solution filtered to remove the precipitated insolubles. The filtered solution, a clear dark green liquid, contained 32.3% solids.

| | |
|---|---|
| Reduced Viscosity $n_{sp}/c$ in acetone solution at 21° C.: | 0.097 Hoeppler Viscosity of 30% by weight acetone solution of dry solids |
| Ratio Sulfone: NSA: Formaldehyde: 1:1:1 | |

EXAMPLE VI

The following procedure was used to evaluate the Example I textile treating agent in the aftertreatment of nylon dyed with acid dyes to improve washfastness.

Application of each textile treating agent was made in individual glass containers to identical portions cut from a large piece of nylon double knit fabric dyed with acid dyes. Uniform agitation and temperature control were provided in a laboratory dyeing machine.

1. Samples of nylon (double knit) fabrics (weighing approximately 250 g) were dyed with the following acid dyes at the indicated concentrations in the Ahiba laboratory dyeing machine using the procedure given below:
   I. Red (Nylanthrene 5 BLF) 2% o.w.f.
   II. Light Blue (Merpacyl Blue 2GA) 2% o.w.f.
   III. Blue (Nylosan Blue N-GL) 2% o.w.f.
   Charged 8000 ml warm water, 80 ml of 5% weight ammonium sulfate solution and 20 ml of 10% by weight solution of nonionic surfactant to the machine and mixed to obtain a bath. Entered sample of nylon fabric into the bath and agitated for 10 minutes at 100°–130° F. Then added a solution of 2 g of each of the above dyes in 1000 ml boiling water to the fabric sample in the bath. Heated the dye bath to 212° F.; held at 212° F. for one hour; added 2 g acetic acid; held at 212° F. for 30 minutes. Drained bath, rinsed dyed nylon fabric, removed the fabric and dried it in an electric dryer.
2. Each sample of dried dyed nylon double knit fabric was treated for 20 minutes at 190° F. in a 300 ml solution containing 0% or 2% solids of textile treating agent based on weight of nylon fabric at pH 4.0 to 4.5 adjusted with acetic acid to obtain a treated dyed nylon sample.
3. The dyed nylon samples were rinsed in warm water (104° F.) and then air dried.
4. The washfastness test was made by adding a 10 g dyed nylon sample to a Laundrometer beaker containing 10 ml of 3% AATC soap solution, 10 ml 3% sodium metasilicate solution and 130 ml tap water. Then samples (2"×2" swatches) of untreated, undyed nylon and cotton were added to the beaker. The beaker was placed in the preheated Laundrometer at 120° F. for 45 minutes and then taken from the Laundrometer. The untreated, undyed samples were removed from the beaker, rinsed in warm water and air dried.
5. Each untreated, undyed, nylon or cotton sample was then read using a D25-M-2 Hunterlab Colorimeter having a one inch aperture to measure bleeding of dyed nylon sample on the untreated, undyed fabric sample. Each untreated, undyed sample was backed with a white cardboard glued to a small weighted board and read without a cover glass. Two readings were made on each untreated, undyed sample, rotating 90° between readings. Two sets of data were obtained. One set of data were the tristimulus values which were Y, X, Z (green, red, blue), the second set were the L, A, B readings where
   L measures the lightness or grayness component of the color of the sample,
   A measures the chromaticity differences in the red-green components of the sample,
   B measures the differences in the yellow-blue components,
   E measures the total color of the sample.
The relationship between the color scales to tristimulus values are:

$$L = 10.0 \sqrt{Y}$$
$$A = \frac{17.5 (1.02 X - Y)}{\sqrt{Y}}$$
$$B = \frac{7.0 (Y - 0.847 Z)}{\sqrt{Y}}$$

(a) Interpretation of Tristimulus Values

The Hunterlab Colorimeter readings of Y, X, Z represent differences between the standard colors Y, X, Z and the Y, X, Z of the samples. That is they show how much of each color has to be added to compensate for the difference between the standard and the sample. The higher the Y, X, Z readings are the more color value exist in the sample. (Less color has to be added to compensate for the difference between standard and sample). From these readings are calculated the $\Delta Y$, $\Delta X$, $\Delta Z$ values $\Delta Y = Y_1$ standard reading - $Y_o$ measured reading
$\Delta X = X_1$ standard reading - $X_o$ measured reading
$\Delta Z = Z_1$ standard reading - $Z_o$ measured reading The $\Delta$ values give the $\Delta Y$, $\Delta X$, $\Delta Z$ tristimulus values of the samples. Lower values of $\Delta Y$, $\Delta X$, $\Delta Z$ show lower colors of the samples.

(b) Interpretation of the Color Scale Values

From the second set of Hunter data the values of $\Delta L$, $\Delta A$, $\Delta B$ and $\Delta E$ were calculated as follows:
$\Delta L = L_1 - L_o$
$\Delta A = A_1 - A_o$
$\Delta B = B_1 - B_o$ $$\Delta E = \sqrt{(\Delta L)^2 + (\Delta A)^2 + (\Delta B)^2}$$

where:
$L_o$, $A_o$, $B_o$ are standard values
$L_1$, $A_1$, $B_1$ are measured values
$\Delta E$ is a calculated value for total color
$\Delta L$ negative value indicates more grayness in the measured sample than in the standard,
$\Delta A$ positive value indicates that the sample is redder than the standard, negative value—greener than standard,
$\Delta B$ positive value indicates that the sample is yellower than the standard, negative value—bluer than standard,
$\Delta E$ is a measure of the total color of the sample with no indication of the character of the color. The above formulas were used to calculate the $\Delta Y$, $\Delta X$, $\Delta Z$, $\Delta L$, $\Delta A$, $\Delta B$ and $\Delta E$ values shown in the table below to determine washfastness of dyed fabric samples which had been aftertreated with Example I textile treating agent within the scope of this invention, and Blank (no textile treating agent) and then washed. These values and those obtained in Example VII are compared at the end of Example VII.

| Washfastness (Dye Fixation) Data 2% Textile Treating Agent | | | | | | | |
|---|---|---|---|---|---|---|---|
| | $\Delta Y$ | $\Delta X$ | $\Delta Z$ | $\Delta L$ | $\Delta A$ | $\Delta B$ | $\Delta E$ |
| I. Red (Nylanthrene 5BLF) | | | | | | | |
| Example I Textile Treating Agent | | | | | | | |

-continued

| | Washfastness (Dye Fixation) Data 2% Textile Treating Agent | | | | | | |
|---|---|---|---|---|---|---|---|
| | ΔY | ΔX | ΔZ | ΔL | ΔA | ΔB | ΔE |
| nylon | 8.41 | 7.41 | 11.86 | −4.63 | 1.73 | 1.85 | 5.28 |
| cotton | 3.16 | 2.93 | 4.86 | −1.72 | 0.32 | 0.75 | 1.90 |
| Blank (No Textile Treating Agent) | | | | | | | |
| nylon | 40.61 | 33.67 | 37.57 | −25.21 | 16.23 | −8.91 | 31.28 |
| cotton | 20.83 | 16.35 | 17.88 | −11.88 | 9.77 | −4.82 | 16.12 |
| II. Light Blue (Merpacyl Blue 2GA) | | | | | | | |
| Example I Textile Treating Agent | | | | | | | |
| nylon 5.51 | 7.40 | 7.97 | −2.48 | −3.94 | 0.99 | 4.76 | |
| cotton | 1.87 | 2.71 | 3.85 | −1.02 | −1.71 | 1.05 | 2.25 |
| Blank (No Textile Treating Agent) | | | | | | | |
| nylon | 30.47 | 34.09 | 15.66 | −18.11 | −9.49 | −15.90 | 25.90 |
| cotton | 12.37 | 15.22 | 6.74 | −6.92 | −6.34 | −5.35 | 10.80 |
| III. Blue (Nylosan Blue N-GL) | | | | | | | |
| Example I Textile Treating Agent | | | | | | | |
| nylon | 15.31 | 17.72 | 9.82 | −8.62 | −5.63 | −5.73 | 11.78 |
| cotton | 1.32 | 2.13 | 3.92 | −0.72 | −1.61 | 1.52 | 2.33 |
| Blank (No Textile Treating Agent) | | | | | | | |
| nylon | 42.97 | 44.18 | 19.19 | −26.96 | −5.14 | −28.02 | 39.22 |
| cotton | 5.92 | 7.15 | 5.03 | −3.25 | −2.64 | −1.28 | 4.38 |

EXAMPLE VII

The following procedure was used to evaluate the Example II through Example V textile treating agents in the aftertreatment of nylon dyed with acid dyes to improve washfastness.

Application of each textile treating agent was made in individual glass containers to identical portions cut from a large piece of nylon double knit fabric dyed with acid dyes. Uniform agitation and temperature control were provided in a laboratory dyeing machine.

1. Samples of nylon (double knit) fabrics (weighing approximately 188–200 g) were dyed with the following acid dyes at the indicated concentrations in the Ahiba laboratory dyeing machine using the procedure given below:
   I. Red (Nylosan Red F-2R)
   II. Black (Nylon Black NDJ)
   III. Blue (Nylosan Blue N-GL)
   Charged 8000 ml warm water, 80 ml of 5% by weight ammonium sulfate solution and 20 ml of 10% by weight solution of nonionic surfactant to the machine and mixed to obtain a bath. Entered sample of nylon fabric into the bath and agitated for 10 minutes at 100°–130° F. Then added a solution of 4 g of each of the above dyes in 1000 ml boiling water to the fabric sample in the bath. Heated the dye bath to 212° F.; held at 212° F. for one hour to complete the dye exhaustion; added 2 g acetic acid and agitated at 212° F. for one hour. Drained bath, rinsed dyed nylon fabric, removed the fabric and dried it in an electric dryer.
2. Each sample of dried dyed nylon double knit fabric was cut into 10 g swatches which were treated with a solution containing 0%, 1% or 2% solids of each textile treating agent based on weight of dyed nylon using steps (a) through (e):
   (a) Adding sufficient treating agent to 300 ml tap water in a 600 ml beaker to obtain a treating agent solution containing 0%, 1% or 2% solids of each agent based on the weight of dyed nylon.
   (b) Adjusting pH of the treating agent solution to 4.0–4.5 with acetic acid.
   (c) Adding 10 g swatch dyed nylon fabric to the solution of acidified treating agent.
   (d) Heating the acidified treating agent solution containing the dyed swatch to 190° F. and holding 20 minutes at 190° F.
   (e) Rinsing the treated dyed swatch in warm water (104° F.) and air drying.
3. The washfastness test was made by adding a 10 g treated dyed nylon swatch to a Laundrometer beaker containing 10 ml of 3% AATC soap solution, 10 ml 3% sodium metasilicate solution and 130 ml tap water. Then samples (2″ × 2″ swatches) of untreated, undyed nylon and cotton were added to the 10 g treated dyed nylon swatch in the beaker. The beaker was placed in the preheated Laundrometer and run for 45 minutes. The untreated, undyed nylon and cotton samples were removed from the beaker, rinsed in warm water and air dried.
4. Each untreated, undyed, nylon or cotton sample was then read using a D25-M-3 Hunterlab Colorimeter with a 1.7 inch port and samples were backed with a white backing plate. Two readings were made on each sample, with a 90° rotation between readings. The readings were then used as in Example VI above to calculate the ΔY, ΔX, ΔZ, ΔL, ΔA, ΔB and ΔE values in table below to determine washfastness of the dyed fabric samples which had been aftertreated with the Example II textile treating agent, which is within the scope of this invention, and Example III textile treating agent, Example IV textile treating agent, Example V textile treating agent, which are outside the scope of this invention, and Blank (no textile treating agent) and then washed.

| | Washfastness (Dye Fixation) Data 1% Textile Treating Agent | | | | | | |
|---|---|---|---|---|---|---|---|
| | ΔY | ΔX | ΔZ | ΔL | ΔA | ΔB | ΔE |
| I. Red (Nylosan Red F-2R) | | | | | | | |
| Example II Textile Treating Agent | | | | | | | |
| nylon | 18.99 | 11.33 | 20.85 | −10.69 | 15.45 | −0.77 | 18.80 |

| | Washfastness (Dye Fixation) Data 1% Textile Treating Agent | | | | | | |
|---|---|---|---|---|---|---|---|
| | ΔY | ΔX | ΔZ | ΔL | ΔA | ΔB | ΔE |
| cotton | 18.92 | 11.31 | 16.09 | −10.65 | 15.34 | −4.14 | 19.12 |
| Example III Textile Treating Agent | | | | | | | |
| nylon | 37.02 | 23.69 | 43.91 | −22.33 | 30.97 | 0.75 | 38.18 |
| cotton | 32.99 | 20.53 | 34.06 | −19.59 | 28.00 | −3.36 | 34.33 |
| Example IV Textile Treating Agent | | | | | | | |
| nylon | 35.85 | 22.79 | 42.07 | −21.53 | 30.02 | 0.34 | 36.94 |
| cotton | 32.28 | 19.90 | 32.25 | −19.10 | 27.65 | −4.10 | 33.85 |
| Example V Textile Treating Agent | | | | | | | |
| nylon | 33.52 | 21.10 | 39.19 | −19.93 | 27.97 | 0.21 | 34.34 |
| cotton | 30.44 | 18.55 | 29.90 | −17.87 | 26.15 | −4.20 | 31.95 |
| Blank (No Textile Treating Agent) | | | | | | | |
| nylon | 44.90 | 29.97 | 55.10 | −28.06 | 37.44 | 2.66 | 46.86 |
| cotton | 39.77 | 26.10 | 44.50 | −24.28 | 32.54 | −1.41 | 40.62 |
| II. Black (Nylon Black NDJ) | | | | | | | |
| Example II Textile Treating Agent | | | | | | | |
| nylon | 13.15 | 11.36 | 15.96 | −7.26 | 3.11 | 0.46 | 7.91 |
| cotton | 3.94 | 3.92 | 2.79 | −2.10 | −0.13 | −1.13 | 2.38 |
| Example III Textile Treating Agent | | | | | | | |
| nylon | 28.62 | 26.48 | 31.03 | −16.70 | 3.39 | −1.67 | 17.12 |
| cotton | 4.79 | 4.65 | 3.69 | −2.56 | 0.03 | −1.18 | 2.82 |
| Example IV Textile Treating Agent | | | | | | | |
| nylon | 19.62 | 17.71 | 22.02 | −11.06 | 3.09 | −0.53 | 11.71 |
| cotton | 3.79 | 3.66 | 2.87 | −2.01 | 0.07 | −0.97 | 2.23 |
| Example V Textile Treating Agent | | | | | | | |
| nylon | 26.60 | 24.47 | 29.31 | −15.40 | 3.44 | −1.18 | 15.82 |
| cotton | 4.25 | 4.12 | 3.45 | −2.26 | 0.06 | −0.94 | 2.44 |
| Blank (No Textile Treating Agent) | | | | | | | |
| nylon | 39.14 | 37.15 | 42.77 | −23.83 | 2.72 | −1.57 | 24.03 |
| cotton | 6.68 | 6.51 | 5.59 | −3.61 | 0.03 | −1.40 | 3.87 |
| III. Blue (Nylosan Blue N-GL) | | | | | | | |
| Example II Textile Treating Agent | | | | | | | |
| nylon | 25.28 | 26.70 | 9.34 | −14.56 | −4.39 | −14.71 | 21.15 |
| cotton | 6.35 | 6.21 | 4.67 | −3.42 | −0.03 | −1.73 | 3.83 |
| Example III Textile Treating Agent | | | | | | | |
| nylon | 42.25 | 42.96 | 14.59 | −26.07 | −4.48 | −29.56 | 39.66 |
| cotton | 6.50 | 7.03 | 2.93 | −3.50 | −1.33 | −2.98 | 4.78 |
| Example IV Textile Treating Agent | | | | | | | |
| nylon | 37.80 | 38.84 | 12.31 | −22.88 | −4.79 | −25.90 | 34.89 |
| cotton | 6.30 | 6.71 | 3.07 | −3.39 | −0.88 | −2.82 | 4.49 |
| Example V Textile Treating Agent | | | | | | | |
| nylon | 42.86 | 43.45 | 14.99 | −26.52 | −4.20 | −30.02 | 40.27 |
| cotton | 7.05 | 7.75 | 2.78 | −3.80 | −1.71 | −3.51 | 5.44 |
| Blank (No Textile Treating Agent) | | | | | | | |
| nylon | 52.45 | 51.95 | 21.78 | −34.05 | −2.16 | −37.95 | 51.03 |
| cotton | 9.55 | 10.45 | 3.50 | −5.21 | −2.23 | −5.00 | 7.55 |

| | Washfastness (Dye Fixation) Data 2% Textile Treating Agent | | | | | | |
|---|---|---|---|---|---|---|---|
| | ΔY | ΔX | ΔZ | ΔL | ΔA | ΔB | ΔE |
| I. Red (Nylosan Red F-2R) | | | | | | | |
| Example II Textile Treating Agent | | | | | | | |
| nylon | 12.69 | 7.60 | 14.60 | −7.00 | 9.84 | −0.10 | 12.07 |
| cotton | 12.80 | 7.96 | 8.83 | −7.06 | 9.33 | −4.06 | 12.38 |
| Example III Textile Treating Agent | | | | | | | |
| nylon | 34.31 | 21.30 | 40.39 | −20.47 | 29.58 | 0.43 | 35.97 |
| cotton | 32.33 | 19.84 | 31.66 | −19.13 | 27.93 | −4.60 | 34.16 |
| Example IV Textile Treating Agent | | | | | | | |
| nylon | 22.05 | 13.05 | 24.84 | −12.57 | 18.58 | −0.56 | 22.44 |
| cotton | 21.23 | 12.46 | 17.25 | −12.05 | 18.00 | −5.29 | 22.29 |
| Example V Textile Treating Agent | | | | | | | |
| nylon | 27.59 | 16.59 | 31.64 | −16.05 | 23.69 | −0.33 | 28.61 |
| cotton | 26.90 | 15.79 | 24.11 | −15.59 | 23.83 | −5.32 | 28.97 |
| Blank (No Textile Treating Agent) | | | | | | | |
| nylon | 44.59 | 29.35 | 54.83 | −27.82 | 38.15 | 2.71 | 47.29 |
| cotton | 39.24 | 25.55 | 43.29 | −23.90 | 32.43 | −1.89 | 40.33 |
| II. Black (Nylon Black NDJ) | | | | | | | |
| Example II Textile Treating Agent | | | | | | | |
| nylon | 10.90 | 10.12 | 13.98 | −6.28 | 2.15 | 0.46 | 6.65 |
| cotton | 4.13 | 4.03 | 2.81 | −2.24 | −0.01 | −1.25 | 2.56 |
| Example III Textile Treating Agent | | | | | | | |
| nylon | 27.09 | 24.96 | 29.04 | −15.75 | 3.48 | −1.82 | 16.23 |
| cotton | 4.34 | 4.16 | 2.40 | −2.22 | 0.16 | −1.67 | 2.78 |
| Example IV Textile Treating Agent | | | | | | | |
| nylon | 13.68 | 12.23 | 16.11 | −7.57 | 2.34 | 0.14 | 7.92 |

-continued

| | Washfastness (Dye Fixation) Data 2% Textile Treating Agent | | | | | | |
|---|---|---|---|---|---|---|---|
| | ΔY | ΔX | ΔZ | ΔL | ΔA | ΔB | ΔE |
| cotton | 3.65 | 3.57 | 2.16 | −1.94 | −0.01 | −1.32 | 2.34 |
| Example V Textile Treating Agent | | | | | | | |
| nylon | 23.79 | 21.54 | 26.16 | −13.63 | 3.75 | −1.07 | 14.17 |
| cotton | 4.14 | 4.02 | 2.81 | −2.21 | 0.03 | −1.26 | 2.54 |
| Blank (No Textile Treating Agent) | | | | | | | |
| nylon | 40.75 | 38.67 | 44.16 | −24.98 | 2.90 | −2.66 | 25.28 |
| cotton | 6.04 | 5.85 | 5.21 | −3.25 | 0.11 | −1.16 | 3.45 |
| III. Blue (Nylosan Blue N-GL) | | | | | | | |
| Example II Textile Treating Agent | | | | | | | |
| nylon | 10.11 | 10.95 | 4.30 | −5.52 | −2.16 | −4.92 | 7.51 |
| cotton | 5.07 | 4.88 | 3.94 | −2.71 | 0.13 | −1.25 | 2.98 |
| Example III Textile Treating Agent | | | | | | | |
| nylon | 34.71 | 35.92 | 10.76 | −20.74 | −4.91 | −23.52 | 31.74 |
| cotton | 5.71 | 6.07 | 2.29 | −3.06 | −0.96 | −2.80 | 4.25 |
| Example IV Textile Treating Agent | | | | | | | |
| nylon | 27.62 | 29.26 | 7.95 | −16.05 | −5.21 | −18.07 | 24.72 |
| cotton | 4.57 | 4.84 | 1.39 | −2.44 | −0.73 | −2.50 | 3.56 |
| Example V Textile Treating Agent | | | | | | | |
| nylon | 34.71 | 36.00 | 11.08 | −20.74 | −5.10 | −23.27 | 31.58 |
| cotton | 5.67 | 6.21 | 1.73 | −3.04 | −1.30 | −3.13 | 4.55 |
| Blank (No Textile Treating Agent) | | | | | | | |
| nylon | 50.52 | 50.24 | 20.02 | −32.46 | −2.64 | −36.53 | 48.93 |
| cotton | 8.9 | 9.79 | 3.35 | −4.83 | −2.19 | −4.59 | 7.01 |

| Evaluation of Washfastness (Dye Fixation) Data 2% Textile Treating Agent | | | | | |
|---|---|---|---|---|---|
| I. Red (Nylanthrene 5 BLF) | | | | | |
| | | Δ E (Total Stain) Example | | Δ A (Red Stain) Example | |
| | | I | Blank | I | Blank |
| | nylon | 5.28 | 31.28 | 1.73 | 16.23 |
| | cotton | 1.90 | 16.12 | 0.32 | 9.77 |
| II. Light Blue (Merpacyl Blue 2GA) | | | | | |
| | | Δ E (Total Stain) | | Δ B (Blue Stain) | |
| | nylon | 4.76 | 25.90 | 0.99 | −15.90 |
| | cotton | 2.25 | 10.80 | 1.05 | −5.35 |
| III. Blue (Nylosan Blue N-GL) | | | | | |
| | | Δ E (Total Stain) | | Δ B (Blue Stain) | |
| | nylon | 11.78 | 39.22 | −5.73 | −28.02 |
| | cotton | 2.33 | 4.38 | 1.52 | −1.28 |

| | Evaluation of Washfastness (Dye Fixation) Data 1% Textile Treating Agent | | | | | |
|---|---|---|---|---|---|---|
| | | Example | | | | |
| | | II | III | IV | V | Blank |
| I. | Red (Nylosan Red F-2R) | | | | | |
| | Δ E (Total Stain) nylon | 18.80 | 38.18 | 36.94 | 34.34 | 46.86 |
| | Δ A (Red Stain) | 15.45 | 30.97 | 30.02 | 27.97 | 37.44 |
| | Δ E (Total Stain) cotton | 19.12 | 34.33 | 33.85 | 31.95 | 40.62 |
| | Δ A (Red Stain) | 15.34 | 28.00 | 27.65 | 26.15 | 32.54 |
| II. | Black (Nylon Black NDJ) | | | | | |
| | Δ E (Total Stain) nylon | 7.91 | 17.12 | 11.71 | 15.82 | 24.03 |
| | Δ L (grayness) | −7.26 | −16.70 | −11.06 | −15.40 | −23.83 |
| | Δ E (Total Stain) cotton | 2.38 | 2.82 | 2.23 | 2.44 | 3.87 |
| | Δ L (grayness) | −2.10 | −2.56 | −2.01 | −2.26 | −3.61 |
| III. | Blue (Nylosan Blue N-GL) | | | | | |
| | Δ E (Total Stain) nylon | 21.15 | 39.66 | 34.89 | 40.27 | 51.03 |
| | Δ B (Blue Stain) | −14.71 | −29.56 | −25.90 | −30.02 | −37.95 |
| | Δ E (Total Stain) cotton | 3.83 | 4.78 | 4.49 | 5.44 | 7.55 |

-continued

| Evaluation of Washfastness (Dye Fixation) Data 1% Textile Treating Agent | | | | | |
|---|---|---|---|---|---|
| | Example | | | | |
| | II | III | IV | V | Blank |
| Δ (Blue Stain) | −1.73 | −2.98 | −2.82 | −3.51 | −5.00 |

| Evaluation of Washfastness (Dye Fixation) Data 20% Textile Treating Agent | | | | | | |
|---|---|---|---|---|---|---|
| | | Example | | | | |
| | | II | III | IV | V | Blank |
| I. | Red (Nylosan Red F-2R) | | | | | |
| | Δ E (Total Stain) nylon | 12.07 | 35.97 | 22.44 | 28.61 | 47.29 |
| | Δ A (Red Stain) | 9.84 | 29.58 | 18.58 | 23.69 | 38.15 |
| | Δ E (Total Stain) cotton | 12.38 | 34.16 | 22.29 | 28.97 | 40.33 |
| | Δ A (Red Stain) | 9.33 | 27.93 | 18.00 | 23.83 | 32.43 |
| II. | Black (Nylon Black NDJ) | | | | | |
| | Δ E (Total Stain) nylon | 6.65 | 16.23 | 7.92 | 14.17 | 25.28 |
| | Δ L (grayness) | −6.28 | −15.75 | −7.57 | −13.63 | −24.98 |
| | Δ E (Total Stain) cotton | 2.56 | 2.78 | 2.34 | 2.54 | 3.45 |
| | Δ L (grayness) | −2.24 | −2.22 | −1.94 | −2.21 | −3.25 |
| III. | Blue (Nylosan Blue N-GL) | | | | | |
| | Δ E (Total Stain) nylon | 7.51 | 31.74 | 24.72 | 31.58 | 48.93 |
| | Δ B (Blue Stain) | −4.92 | −23.52 | −18.07 | −23.27 | −36.53 |
| | Δ E (Total Stain) cotton | 2.98 | 4.25 | 3.56 | 4.55 | 7.01 |
| ΔB (Blue Stain) | | −1.25 | −2.80 | −2.50 | −3.13 | −4.59 |

| Visual Observation of Washfastness (Dye Fixation) Data 2% Textile Treating Agent | | | |
|---|---|---|---|
| Example | Red Stain | Blue Stain | Grayness |
| Nylon | | | |
| I | slight pink | slight blue | |
| II | light pink | very minor | off white |
| III | red stain | dark blue stain | gray |
| IV | dark pink | dark blue stain | off white |
| V | red stain | dark blue stain | gray |
| Blank | dark red | very dark blue stain | heavy gray |
| Cotton | | | |
| I | very minor | very minor | |
| II | light pink | no stain | very minor |
| III | red stain | very minor | very minor |
| IV | dark pink | very minor | very minor |
| V | red stain | very minor | very minor |
| Blank | dark red | slight | slight |

| Visual Observation of Washfastness (Dye Fixation) Data 1% Textile Treating Agent | | | |
|---|---|---|---|
| Example | Red Stain | Blue Stain | Grayness |
| Nylon | | | |
| II | dark pink | light blue | off white |
| III | red stain | dark blue | gray |
| IV | red stain | dark blue | light gray |
| V | red stain | dark blue | gray |
| Blank | dark red stain | heavy blue | dark gray |
| Cotton | | | |
| II | dark pink | slight | off white |
| III | red stain | slight | minor |
| IV | red stain | slight | off white |
| V | red stain | slight | off white |
| Blank | dark red stain | very light | off white |

Examples VI and VII show that Example I and Example II textile treating agents are effective as dye fixation agents when used at 1% owf and are more effective at 2% owf. Further, these examples show that Examples III, IV and V textile treating agents are not satisfactory. Unsatisfactory results were very pronounced with red colors on both nylon and cotton and with blue and black colors on nylon.

While the invention has been described with reference to cerain specific embodiment thereof, it is understood that it is not to be so limited since alterations and changes may be made therein which are within the full and intended scope of the appended claims.

What is claimed is:

1. In a process for dyeing nylon textile material selected from the group consisting of nylon and cotton blends thereof, the improvement comprising treating the textile material after dyeing with a water soluble polymeric textile treating agent in an amount sufficient to improve washfastness, the textile treating agent comprising a reaction product of one mole of dihydroxy diphenyl sulfone, formaldehyde and naphthalenesulfonic acid wherein a 30% by weight acetone solution of the textile treating agent has a reduced viscosity of from about 0.225 to about 2.275 at 21° C.

2. The process of claim 1 wherein the textile treating agent comprises a reaction product of one mole of dihydroxy diphenyl sulfone with from about 0.85 to about 1.10 mole of formaldehyde and from about 0.9 to about 1.1 mole of naphthalenesulfonic acid.

3. The process of claim 1 wherein the textile treating agent comprises a reaction product of one mole of dihydroxy diphenyl sulfone with from about 0.90 to about 0.95 mole of formaldehyde and from about 0.95 to about 1.00 mole of naphthalenesulfonic acid.

4. The process of claim 1 wherein from about 1 to about 5% of the textile treating agent owf is applied to dyed nylon textile material and dried.

5. The process of claim 1 wherein from about 1 to about 2% of the textile treating agent owf is applied to dyed nylon textile material and dried.

6. The process of claim 1 wherein about 1% of the textile treating agent owf is applied to dyed nylon textile material and dried.

7. The process of claim 1 wherein the textile material is nylon.

8. The process of claim 1 wherein the textile material is a nylon and cotton blend.

9. The process of claim 1 wherein concentration of the textile treating agent in aqueous solution is 70% by weight.

* * * * *